United States Patent [19]

Leif

[11] 4,250,830
[45] Feb. 17, 1981

[54] SWINGING BUCKETS

[76] Inventor: Robert C. Leif, 1030 Mariposa Ave., Coral Gables, Fla. 33146

[21] Appl. No.: 81,324

[22] Filed: Oct. 3, 1979

[51] Int. Cl.³ .................... G01N 9/30; B05C 11/12
[52] U.S. Cl. ..................... 118/52; 422/72; 422/101; 422/104; 118/401; 233/14 R
[58] Field of Search ............... 427/2, 240; 118/52–56, 118/401, 412, 415; 422/72, 101, 104; 233/26, 12, 14 R; 210/377

[56] References Cited

U.S. PATENT DOCUMENTS

| 2,114,748 | 4/1938 | Prausnitz | 422/101 |
| 4,119,407 | 10/1978 | Goldstein et al. | 422/72 |
| 4,143,187 | 3/1979 | Pilgrim et al. | 118/415 |
| 4,192,250 | 3/1980 | van Duijn | 422/72 |

OTHER PUBLICATIONS

Leif, R. C. et al., ACTA Cytologica, vol. 19, No. 2, (1975), pp. 159–168.
Leif, R. C. et al., The Journal of Histochemistry and Cytochemistry, vol. 25, No. 7, (1977), pp. 538–543.
Otto, K. et al., Analytical and Quantitive Cytology, vol. 1, No. 2, (1979), pp. 127–135.
Leif, R. C. et al., Journal of Histochemistry and Cytochemistry, vol. 19, (1971), pp. 203–215.
Dunlap, L. A. et al., Journal of Histochemistry and Cytochemistry, vol. 23, (1975), pp. 369–377.
Vinograd, J. R. et al., Proc. N.A.S., vol. 49, (1963), pp. 902–910.
Pickels, E. G. et al., Proc. N.A.S., vol. 38, (1952), pp. 943–948.

Primary Examiner—William F. Smith
Assistant Examiner—Chris Konkol
Attorney, Agent, or Firm—William A. Newton

[57] ABSTRACT

Disclosed is a centrifugal cytology swinging bucket for providing multiple dispersions of fixed cells or other particles onto a microscope slide or similar substrate, the bucket comprising a slide holder for receiving a slide and a transparent sample block having a sample chamber with drill holes for fluid communication between fixative cups, such fixative cups having porous frits therein. The bucket further comprises a pair of holddowns each having an eccentric cam and a lever protruding therefrom.

7 Claims, 5 Drawing Figures

SWINGING BUCKETS

FIELD OF THE INVENTION

The present invention relates to centrifugal cytology swinging buckets for providing multiple dispersions of cells or other particles onto a microscope slide or similar substrate.

DESCRIPTION OF PRIOR ART

The microscopic analysis of fixed stained dispersions of cells and other particles on glass microscope slides and other substrates is presently a well-established clinical procedure. Swinging buckets have been developed in the prior art as one means for providing these fixed stained dispersions. The development of swinging buckets is illustrated in the following articles: R. C. Leif, et al., "Centrifugal Cytology IV—The Preparation of Fixed Stained Dispersions of Gynecological Cells", ACTA CYTOLOGICA, Volume 19, No. 2, (1975), pp. 159-168; R. C. Leif, et al., "Optimization of the Binding of Dissociated Exfoliated Cervicovaginal Cells to Glass Microscope Slides", THE JOURNAL OF HISTOCHEMISTRY AND CYTOCHEMISTRY, Volume 25, No. 7, (1977), pp. 538-543; and K. Otto et al., "Components and Results of a New Preparation Technique for Automated Analysis of Cervical Samples", ANALYTICAL AND QUANTITATIVE CYTOLOGY, Volume 1, No. 2, (1979), pp. 127-135.

In these prior art swinging bucket arrangements, the cells are first centrifuged onto a slide without loss of the supernatant suspending medium. Then, if necessary or desirable, excess suspending medium is removed via a drill hole which is in direct contact with the medium just above the slide. Finally fixative is over-layered onto the cells, and the centrifugal field is applied. In the first development of the technique (R. C. Leif, H. N. Easter, R. L. Warters, R. A. Thomas, L. A. Dunlap and M. F. Austin: "Centrifugal Cytology I. A Quantitative Technique for the Preparation of Glutaraldehyde-Fixed Cells for the Light and Scanning Electron Microscope", JOURNAL OF HISTOCHEMISTRY AND CYTOCHEMISTRY, Volume 19, (1971), pp. 203-215) the fixative fluid was very slowly and carefully delivered with a single syringe in order not to dislodge the cells from the slide. Fixed dislodged cells would not be expected to adhere to the slide since equivalent cells fixed in suspension did not. The next technique was to perform the overlayering with a multipipeting machine (L. A. Dunlap, R. L. Warters and R. C. Leif: "Centrifugal Cytology III. The Utilization of Centrifugal Cytology for the Preparation of Fixed Stained Dispersions of Cells Separated by BSA Buoyant Density Centrifugation.", JOURNAL OF HISTOCHEMISTRY AND CYTOCHEMISTRY, Volume 23, (1975), pp. 369-378) which permitted very accurate control of the flow of fixative and expedited the handling of samples by permitting the fixative to be added to more than one sample chamber. However, the use of the pipeting machine was not totally satisfactory and it was superseded by the use of a drill hole of controlled bore which was to deliver the fixative after the centrifugal field was applied and after all of the cells were firmly pressed against the slide. The small diameter drill hole was used as a barrier to the flow of fluid, such a barrier being caused by the entrapment of air in the drill hole. A similar design which used a shallow channel had previously been employed with the analytical ultracentrifuge by J. R. Vinograd, R. Bruner, R. Kent and J. Weigle: "Band-Centrifugation of Macromolecules and Viruses in Self-Generating Density Gradients", PROCEEDINGS OF THE NATIONAL ACADEMY OF SCIENCE USA, Volume 49, (1963), pp. 902-910. When a centrifugal force is applied to the swinging bucket, the hydrostatic pressure forces the trapped air out, allowing the solutions to flow through the drill hole. However, in the case of Centrifugal Cytology, holes which retarded the flow of fixative often clogged, thus rendering the system unreliable. Large drill holes did not retard the flow of fixative.

Besides drill holes or micro-channels, deformable synthetic boundary valves (E. G. Pickels, W. F. Harrington and H. K. Schachman, "An Ultracentrifuge Cell for Producing Boundaries Synthetically by a Layering Technique", PROCEEDINGS OF THE NATIONAL ACADEMY OF SCIENCE USA, Volume 38, (1952), pp. 943-948) have been employed.

In order to securely attach the component parts of the swinging bucket, such as a sample block to the microscope slide, manually operated hold-down clamps are rotated 180° and a socket head screw must be tightened manually with a wrench. Moreover, the sample blocks of the swinging buckets are made out of an opaque material which makes it difficult to visually determine fluid levels therein.

SUMMARY OF THE INVENTION

The present invention relates to an improved centrifugal cytology swinging bucket for providing multiple dispersions onto a microscope slide or other substrate wherein the bucket comprises a substrate carrier adapted for receiving the substrate and a sample block, the block having fixative cups in fluid communication with sample chambers. The improvement of the present invention comprises providing a porous frit which acts as a fluid barrier to greatly retard the flow of fluid between the fixative cup and the sample chamber, but permits the rapid overlayering of the cells when a centrifugal force is applied. The improvement of the present invention further comprises providing hold-downs in the form of eccentric cams which are held in a compressing relationship with the sample block by the applied centrifugal force. The improvement of the present invention further comprises forming the sample block of transparent, hard elastomeric material, so that the fluid levels are readily visible and the sample block will slightly deform adjacent the substrate to form and maintain a sealed relationship to it.

BRIEF DESCRIPTION OF THE DRAWINGS

Further objects and advantages of the present invention will become apparent as the following description proceeds, taken in conjunction with the accompanying drawings in which.

DESCRIPTION OF THE PREFERRED EMBODIMENT

Figure 1:
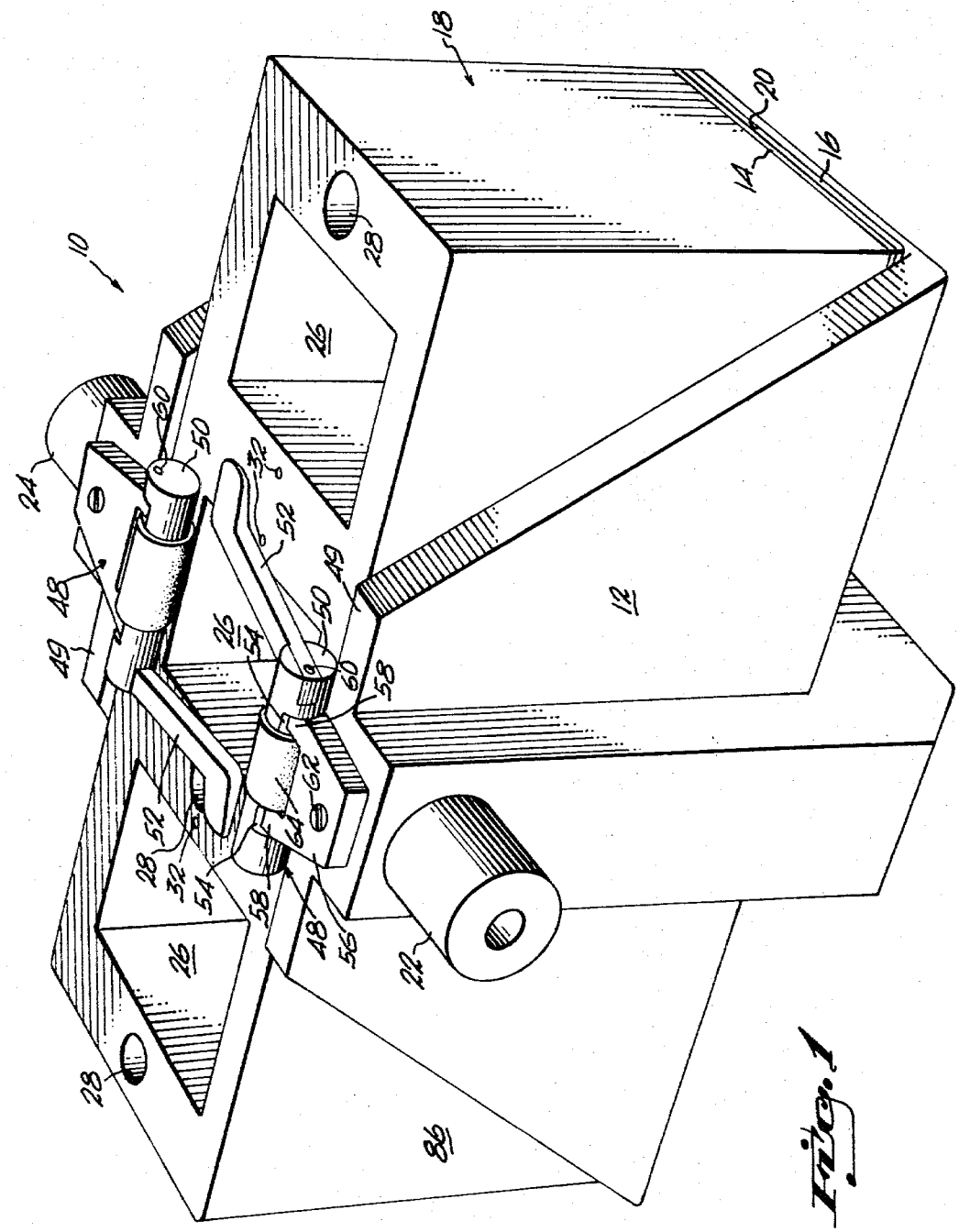
FIG. 1 is a perspective view of the swinging bucket embodying the present invention.

Referring to FIG. 1, a centrifugal cytology swinging bucket is identified generally by numeral 10. The swinging bucket 10 comprises a slide carrier 12 that supports a conventional microscope slide 14 or other substrate, a gasket 16, and a sample block 18. As illustrated in the cross-sectional view of FIG. 2, the microscope slide 14 and the gasket 16 are held between the sample block 18 and the slide carrier 12. In one implementation of the swinging bucket the gasket 16 is placed on the flat surface 20 of the slide carrier 12. On top of the gasket 16, the slide 14, typically a glass microscope slide, is placed. The sample block 18 is placed upon the slide 14. Then this arrangement is fixed by the present invention in a manner to be described hereinafter. The swinging bucket 10 is disassembled in reverse order.

Figures 2, 3:
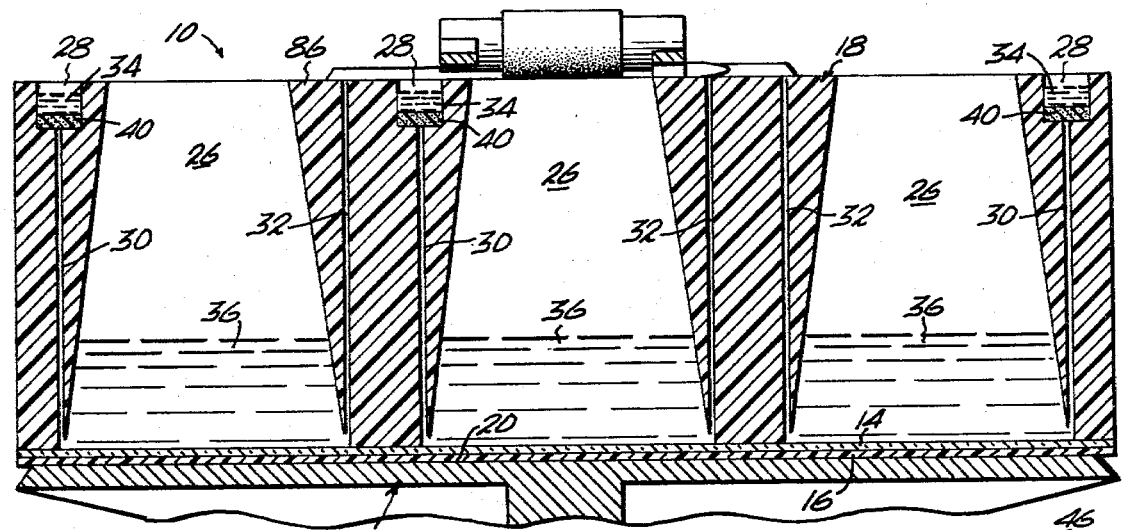
FIG. 2 is a cross section of the swinging bucket of FIG. 1.
FIG. 3 is an enlarged fragmentary view of alternative embodiment of porous frit of FIG. 2.

Referring to FIGS. 1 and 2, a pair of carrier mounts 22 and 24 are used to pivotally mount the slide carrier 12 so that the swinging bucket pivots outward when a centrifugal field is applied by a conventional centrifuge. A plurality of sample chambers 26 are integrally formed in the sample block 18. The contents of each of the sample chambers 26 are centrifuged onto the slide 14. The number of sample chambers varies, with the prior art arrangements typically having three to twelve. As shown in the cross-sectional view of FIG. 2, a plurality of fixative cups 28 are formed in the sample block 18. Each fixative cup 28 is connected to the corresponding sample chamber 26 by a small fluid distributing drill hole 30. Oppositely disposed to drill hole 30, is a fluid aspirating drill hole 32, which likewise is in fluid communication with the sample chamber 26. The volume of liquid in the sample chamber 26 is reduced after centrifugation by aspirating through a needle which fits tightly in the holes 32.

Referring to FIG. 2, in operation a dilute suspension of cells or other particles is added to at least one of the sample chambers 26. After the cells have been deposited on the slide 14, well known fixatives 34 (or in certain cases other solutions) are added to the fixative cups 28. Excess solution 36 which would either inhibit the drainage from the fixative cups 28 or interfere with other processes is removed via the small drill holes 32. The fixative 34 is conveyed to the surface of the slide 14 via the drill hole 30. Hence, multiple dispersions can be deposited on a single slide 14, and the suspending medium and all other solutions are sealed into the sample chambers 26. Consequently cells in the suspending medium are not air dried. More specifically, the swinging bucket 10 permits the fixative 34 or other solution to be brought down to the surface of the slide 14 after the initial sedimentation of the cells in the sample chamber 26 and also allows any excess solution to be removed from the sample chamber 26.

Referring to FIG. 2, one aspect of the improvement of the present invention comprises providing a synthetic boundary valve in the form of a porous frit 40, preferably formed of plastic. The frits 40 are disposed at the bottom of the fixative cups 28. The frit 40 serves as a barrier to the flow of liquid therethrough when a centrifugal force is not being applied to the swinging bucket 10. When a centrifugal force is applied to the swinging bucket 10, the hydrostatic pressure forces the fluid to penetrate the frit 40.

Referring to FIG. 3, an alternative construction for the frit 40 is shown which allows the frit 40 to be disposable and easily removed from the fixative cup 28. A wall portion 42 of the frit 40 integrally connects with a base portion 44, such base portion 44 being disposed at the bottom of the fixative cup 28. The wall portion 42 of the frit 40 is dimensioned and configured to conform to and to extend up the walls of the fixative cup 28. Moreover, the frit 40 protrudes above the upper extremities of the fixative cups 28 to define a ledge portion 46 of the frit 40. By manually grasping the wall portion 42 and/or the ledge portion 46, the frit 40 can be readily removed.

Referring to FIG. 1, another aspect of the present invention comprises providing a pair of holddowns 48 disposed on opposed upper longitudinal edges 49 of the slide carrier 12. Each holddown 48 employs an eccentric cam 50 having a lever 52 protruding therefrom. Each eccentric cam 50 is pivotally secured, in a pair of integrally formed slots 54, to a forked, mounting tongue 56, having a pair of prongs 58. A pivot pin 60 is disposed in traversing relationship through the slots 54 of the cam 50, and the prongs 58 of the tongue 56, so as to provide the above described pivotal relationship. Hence, the holddowns 48 act as a hinge, with the eccentric cam 50 being one element of the hinge and the forked tongue 56 being the other element of the hinge. Each of the pair of tongues 56 is rotatably secured to the upper longitudinal edges 49 of the slide carrier 12 by conventional means, such as pivot bolt 62. The rotatable mounting of the holddowns 48 allows for the same to be rotated outward, for example, when the sample block 18 is slipped into the slide carrier 12. A sleeve 64 can be optionally mounted in surrounding relationship to the cam 50 between the prongs 58 of the tongue 56. By virtue of this arrangement, when the cam 50 is rotated, the sleeve 64 stays in a relatively fixed disposition with respect to the underlying sample block 18. Hence, the sleeve 64 prevents abrasions on the top of the sample block 18 that could normally occur with the frictional, abrasive engagement of the cam 50 with the top of the sample block 18. Rotation of the holddowns 48 permits the sample block 18 and the slide 14 to be tightly secured to the carrier 12. Consequently, the lever 52 can initially be manually rotated downward to obtain a relatively tight relationship between the sample block 18 and the slide 14. Once a centrifugal force is applied to the swinging bucket 10, the centrifugal force acts on the lever 52 to propel the lever 52 downward, which in turn further compresses the sample block 18 on the slide 14, thereby providing an even tighter relationship. Hence, the holddowns 48 serve as a self tightening device and maintain the above-described tight relationship while the centrifugal force is being applied.

Figure 4:
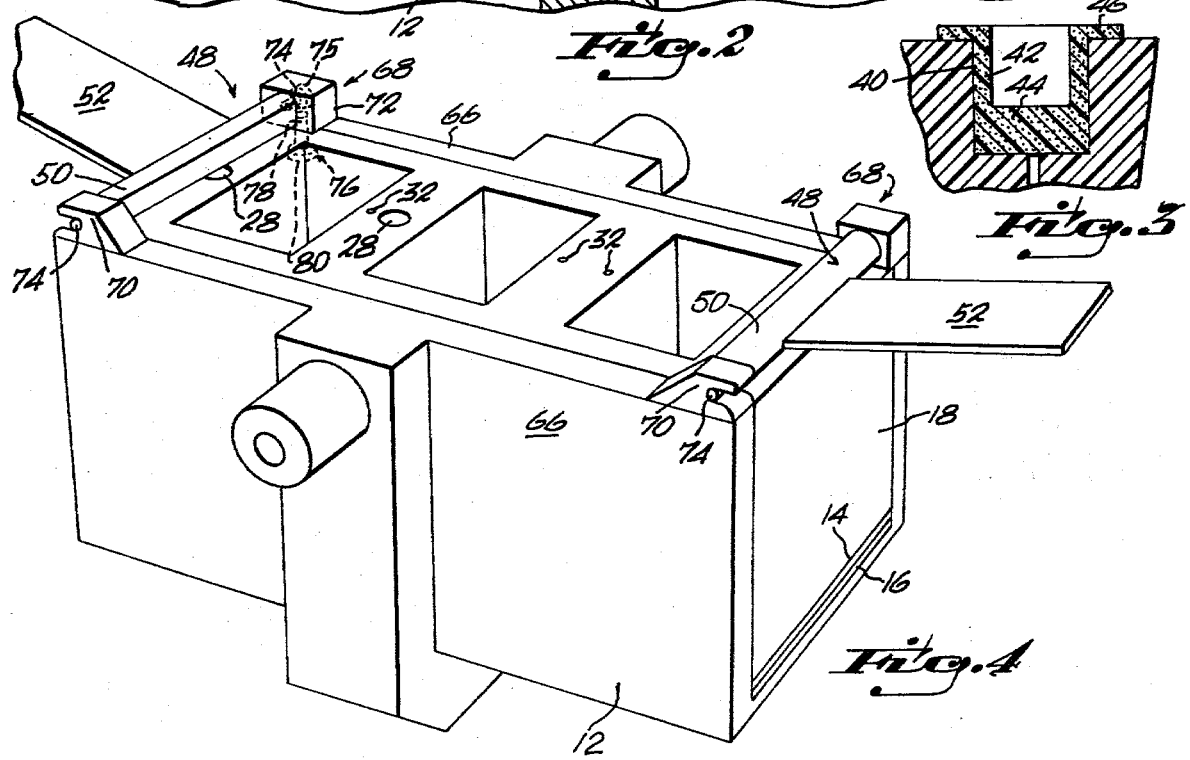
FIG. 4 is a perspective view of another embodiment of the swinging bucket.
Figure 5:
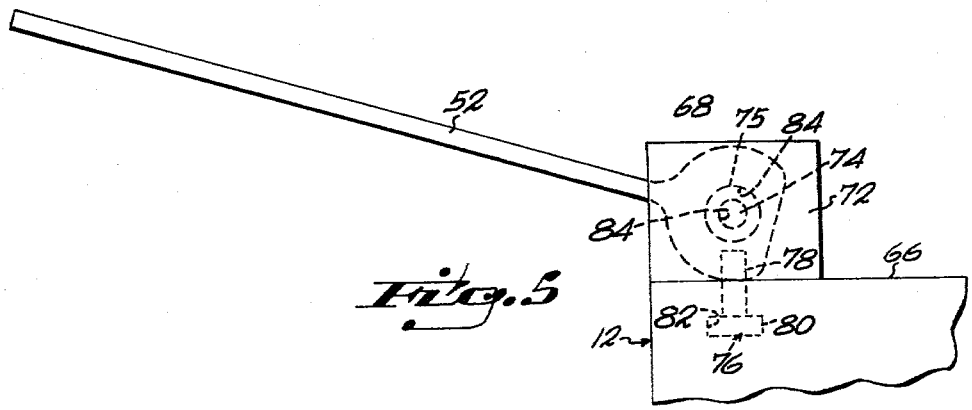
FIG. 5 is an enlarged fragmentary view of the hold-down of FIG. 4.

Referring to FIG. 4, there is illustrated an alternative embodiment for the holddowns 48. More specifically, the sides 66 of the slide carrier 12 are extended so as to provide mounting positions for the pair of holddowns 48 on opposed lateral ends 68 of the slide carrier 12. One of the pair of sides 66 has a pair of fixed catches 70 mounted to the upper opposed ends thereof. The other side 66 has a pair of mounting blocks 72 rotatably attached to the upper opposed ends thereof. Each of the pair of cams 50, with its protruding lever 52, has a pair of integrally formed extension knobs 74 extending from each end thereof, such knobs defining therebetween the longitudinal pivotal axis for the cam 50. As illustrated in more detail in the enlarged, fragmentary view of FIG. 5, each of the mounting blocks 72 are rotably mounted to the slide carrier 12 by a pivoting member 76. Ideally, the pivoting member 76 is rigidly secured at one end portion 78 in the mounting block 72, while an opposed, enlarged end portion 80 can slidably rotate within a chamber 82. Each of the mounting blocks 72 has an aperture 84 formed therein which is cooperatively aligned with the corresponding fixed catch 70 on the opposed side 66. One of the extension knobs 74 of the cam 50 has an enlarged portion 75 which is used to rotatably mount one end of the cam 50 in non-detachable relationship inside the aperture 84, with the other extension knob 74 being adapted to snap into the corresponding fixed catch 70. It should be appreciated that the holddown 48, when free of the fixed catch 70, can be rotated about the pivoting member 76, so as to allow the placement of the various components inside of the slide carrier 12.

Referring to FIGS. 1 and 2, a third aspect of the present invention comprises forming the sample block 18 of a transparent material 86. The use of the transparent material 86 allows for viewing the fluid levels in the fixative cups 28 and the sample chambers 26. Moreover, the sample block 18 is formed of a hard, but locally deformable material 86 which seals against the slide 14. Hence, the material 86 takes the form of a transparent, hard elastomeric urethane, which provides visibility, while slightly deforming to seal against the slide 14.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A centrifugal cytology bucket for providing multiple dispersions onto a substrate, wherein said bucket includes a substrate carrier adapted for pivotal mounting and further includes a sample block having at least one sample chamber formed therein with a fluid distributing hole defining a liquid path between the sample chamber and a fixative cup, wherein the improvement comprises:
   a porous frit disposed in said fixative cup for substantially retarding the fluid flow from the fixative cup to the sample chamber when there is no centrifugal force applied while permitting a substantial fluid flow when a centrifugal force is applied.

2. In the bucket of claim 1,
said porous frit being disposed at the base of the fixative cup across the fluid distributing hole.

3. In the bucket of claim 2,
said porous frit being dimensioned and configured to conform to the interior surfaces of the fixative cup and to extend above the fixative cup so as to define a ledge.

4. In the bucket of claim 1, wherein a pair of opposed holddowns are mounted on the substrate carrier for securely compressing the sample block on the substrate, the improvement further comprising:
   each said holddown comprising a pivotally mounted eccentric cam with a lever protruding therefrom, whereby a centrifugal force applied to said lever maintains the sample block in a tight, sealed relationship to the substrate.

5. In the bucket of claim 1,
the sample block being composed of a transparent material, whereby visual determinations of fluid levels can be achieved.

6. In the bucket of claim 1,
the sample block being composed of a hard, elastomeric material, whereby the sample block slightly deforms in a region adjacent the substrate so as to form a seal therebetween.

7. In the bucket of claim 4,
said eccentric cam having a sleeve disposed in surrounding relationship thereto for preventing abrasions of the sample block.

* * * * *